US011033641B2

(12) United States Patent
Andrés-Gil et al.

(10) Patent No.: US 11,033,641 B2
(45) Date of Patent: *Jun. 15, 2021

(54) RADIOLABELLED MGLUR2/3 PET LIGANDS

(71) Applicant: Janssen Pharmaceutica NV, Beerse (BE)

(72) Inventors: José Ignacio Andrés-Gil, Madrid (ES); Michiel Luc Maria Van Gool, Madrid (ES); Guy Maurits R Bormans, Rotselaar (BE); Joost Verbeek, Enkhuizen (NL)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/061,437

(22) PCT Filed: Dec. 16, 2016

(86) PCT No.: PCT/EP2016/081542
§ 371 (c)(1),
(2) Date: Jun. 12, 2018

(87) PCT Pub. No.: WO2017/103182
PCT Pub. Date: Jun. 22, 2017

(65) Prior Publication Data
US 2020/0306389 A1    Oct. 1, 2020

(30) Foreign Application Priority Data
Dec. 18, 2015 (EP) ..................................... 15201240

(51) Int. Cl.
| *A61K 51/00* | (2006.01) |
| *A61M 36/14* | (2006.01) |
| *A61K 51/04* | (2006.01) |
| *C07B 59/00* | (2006.01) |
| *C07D 487/04* | (2006.01) |

(52) U.S. Cl.
CPC ........ *A61K 51/0459* (2013.01); *C07B 59/002* (2013.01); *C07D 487/04* (2013.01)

(58) Field of Classification Search
CPC . A61K 51/0459; C07B 59/002; C07D 487/04
USPC ...................................................... 424/1.89
See application file for complete search history.

(56) References Cited

U.S. PATENT DOCUMENTS

| 10,112,949 | B2* | 10/2018 | Andres-Gil | ............ | A61P 25/18 |
| 2001/0011087 | A1 | 8/2001 | Wehner et al. | | |
| 2003/0027807 | A1 | 2/2003 | Wehner et al. | | |
| 2005/0107412 | A1 | 5/2005 | Maw et al. | | |
| 2013/0310555 | A1 | 11/2013 | Chong | | |
| 2015/0005313 | A1 | 1/2015 | Brodney et al. | | |

FOREIGN PATENT DOCUMENTS

| EP | 0756200 B1 | 1/1997 |
| EP | 2327704 A1 | 6/2011 |
| EP | 2666775 A1 | 11/2013 |
| JP | 2007507446 | 3/2007 |
| JP | 2008503510 | 2/2008 |
| JP | 2008530042 | 8/2008 |
| JP | 2008534455 | 8/2008 |
| JP | 2012501352 | 1/2012 |
| JP | 2013189395 | 9/2013 |
| JP | 2016124810 | 7/2016 |
| WO | 2002/096873 A1 | 12/2002 |
| WO | 2005/002552 A2 | 1/2005 |
| WO | 2005/040171 | 5/2005 |
| WO | 2005/061507 A1 | 7/2005 |
| WO | 2005/123738 | 12/2005 |
| WO | 2006/030847 A1 | 3/2006 |
| WO | 2006/050803 A1 | 5/2006 |
| WO | 2006/084634 | 8/2006 |
| WO | 2006/099972 | 9/2006 |
| WO | 2007/084314 A2 | 7/2007 |
| WO | 2007092416 A2 | 8/2007 |
| WO | 2008/001115 A2 | 1/2008 |
| WO | 2008/141239 A1 | 11/2008 |
| WO | 2009/095872 A2 | 8/2009 |
| WO | 2009/118292 A1 | 10/2009 |
| WO | 2009/130232 A1 | 10/2009 |
| WO | 2010/025890 | 3/2010 |

(Continued)

OTHER PUBLICATIONS

Alfonso R. Gennaro, Pharmaceutical Sciences, Remington's, 1990, pp. 1435-1712, 18th edition.
Alper, et al., Agonist-Stimulated [35S]GTBgS Binding, Current Protocols in Pharmacology, 1998, pp. 1-10, vol. 2 Issue 6.
Andres, et al., Synthesis, Evaluation, and Radiolabeling of New Potent Positive Allosteric Modulators of the Metabotropic Glutamate Receptor 2 as Potential Tracers for Positron Emission Tomography Imaging, Journal of Medicinal Chemistry, Sep. 20, 2012, pp. 8685-8699, vol. 55.
Bigotti, et al, Synthesis of C[CH(RF)NH]Gly-peptides: The dramatic effect of a single fluorine atom on the diastereocontrol of the key aza-Michael reaction, Journal of Fluorine Chemistry, Jun. 27, 2008, pp. 767-774, 129.

(Continued)

*Primary Examiner* — Michael G. Hartley
*Assistant Examiner* — Sean R Donohue
(74) *Attorney, Agent, or Firm* — Fay Kaplun & Marcin, LLP

(57) ABSTRACT

The present invention relates to novel, radiolabelled mGluR2/3 ligands, selective 5 versus other mGlu receptors, which are useful for imaging and quantifying the metabotropic glutamate receptors mGlu2 and 3 in tissues, using positron-emission tomography (PET). The invention is also directed to compositions comprising such compounds, to processes for preparing such compounds and compositions, to the use of such compounds and compositions for imaging a tissue, cells or a mammal, in vitro or 10 in vivo and to precursors of said compounds.

12 Claims, 4 Drawing Sheets

(56) References Cited

FOREIGN PATENT DOCUMENTS

| WO | 2010/130423 A1 | 11/2010 |
|----|----------------|---------|
| WO | 2010/130424 | 11/2010 |
| WO | 2012/035078 A1 | 3/2012 |
| WO | 2012/062752 A1 | 5/2012 |
| WO | 2012/083224 A1 | 6/2012 |
| WO | 2012/143726 A1 | 10/2012 |
| WO | 2013/012915 A1 | 1/2013 |
| WO | 2013/012918 A1 | 1/2013 |
| WO | 2013/066736 A1 | 5/2013 |
| WO | 2013/154878 A1 | 10/2013 |
| WO | 2013/156869 A1 | 10/2013 |
| WO | 2013/174822 A1 | 11/2013 |
| WO | 2013/192343 A1 | 12/2013 |
| WO | 2013/192347 A1 | 12/2013 |
| WO | 2013/192350 A1 | 12/2013 |
| WO | 2014/008197 A1 | 1/2014 |
| WO | 2014/064028 A1 | 5/2014 |
| WO | 2014/195311 | 12/2014 |
| WO | 2014/207082 A1 | 12/2014 |
| WO | WO2014/195311 | 12/2014 |
| WO | 2016/016381 A1 | 2/2016 |
| WO | 2016/016382 A1 | 2/2016 |
| WO | 2016/016383 A1 | 2/2016 |
| WO | 2016/016395 | 2/2016 |
| WO | 016380 | 2/2016 |
| WO | WO2016/016395 A1 | 2/2016 |
| WO | 2016/087487 A1 | 6/2016 |
| WO | 2016/087489 A1 | 6/2016 |
| WO | 2017/103179 A1 | 6/2017 |
| WO | 2017/103182 A1 | 6/2017 |

OTHER PUBLICATIONS

Cai, et al., Chemistry with [18F]Fluoride Ion., Europeon Journal of Organic Chemistry, May 6, 2008, pp. 2853-2873, Page number.
Cid, et al., Discovery of 1,4-Disubstituted 3-Cyano-2-pyridones: A New Class of Positive Allosteric Modulators of the Metabotropic Glutamate 2 Receptor, Journal of Medicinal Chemistry, Feb. 24, 2012, pp. 2388-2405, vol. 55, American Chemical Society.
D. S. Ermolat'Ev et al, One-pot microwave-assisted protocol for the synthesis, Mol Divers, Aug. 26, 2010, pp. 491-496, vol. 15.
Dinklo Theo et al, Characterization of 2-[[4-Fluoro-3-(trifluoromethyl)phenyl]amino]-4-(4-pyridinyl)-5-thiazolemethanol (JNJ-1930942), a Novel Positive Allosteric Modulator of the 7 Nicotinic Acetylcholine Receptor☐S, The Journal of Pharmacology and Experimental Therapeutics, 2011, pp. 560-574, vol. 336 No. 2.
Embrechts S. et al, Longitudinal characterisation of the TauPS2APP mouse model of Alzheimer's disease in a two trial discrimination task of visuo-spatial recognition memory, 45th European Brain and Behaviour Society Meeting Sep. 6-9, 2013 Munich, Sep. 6, 2009, p. 202, not applicable.
Farinha, et al., Research Paper Molecular determinants of positive allosteric modulation of the human metabotropic glutamate receptor 2, British Journal of Pharmacology, 2015, pp. 2383-2396, vol. 172.
Ferraguti, et al, Metabotropic glutamate receptors, Cell & Tissue Research, Jul. 18, 2006, pp. 483-504, vol. 326.
Gilfillian, et al, Synthesis and biological evaluation of novel 2,3-dihydro-1H-1,5-benzodiazepin-2-ones; potential imaging agents of the metabotropic glutamate 2 receptor, Med. Chem. Commun., May 29, 2013, pp. 1118-1123, vol. 4 Issue 7.
Goeldner, et al., Cognitive impairment in major depression and the mGlu2 receptor as a therapeutic target Neuropharmacology, Aug. 3, 2013, pp. 337-346, vol. 64.
Guy A. Higgins et al., Pharmacological manipulation of mGlu2 receptors influences, Neuropharmacology, 2004, pp. 907-917, vol. 46.
Hackam, et al, "Translation of Research Evidence From animals to Humans", JAMA, vol. 296 (14): pp. 1731-1732 (2006).
Hickinbottom, English translation of the relevent from reaction of organic complonents, Reactions of organic compounds, 1939, pp. 360-362, Page Number.
Hoffmann-La Roche, ARTDeCo study: A Study RO4995819 in Patients with Major Depressive Disorder and Inadequate Response to Ongoing Antidepressant Treatmnet, ClinicialTrials.gov, Oct. 24, 2011, Placebo, NCT01457677.
Kelmendi, et al, The role of the Glutamatergic system in the pathophysiology and treatment of mood disorders, Primary Psychiatry, 2006, pp. 80-86, vol. 13 Issue 10.
Koike, et al., Role of BDNF/TrkB signaling in antidepressant-like effects of a group II metabotropic glutamate receptor antagonist in animal models of depression, Behavioural Brain Research, 2013, pp. 48-52, vol. 238.
Li Jingjie et al, Palladium-Catalyzed Oxidative Rearrangement of Tertiary Allylic Alcohols to Enones with Oxygen in Aqueous Solvent, Organic Letters, Oct. 3, 2014, pp. 5370-5373, No. 16.
Malkov, et al., On the Selective N-Methylation of BOC-Protected Amino Acids., J. Org. Chem., Oct. 7, 2009, pp. 8425-8427, vol. 74 Issue 21.
Moscow., Chemical Encyclopedia, Soviet encyclopedia, 1988, pp. 242-243, vol. 1.
Niswender, et al., Metabotropic Glutamate Receptors: Physiology, Pharmacology, and Disease, Annu.Rev. Pharmacol.Toxicol., 2010, pp. 295-322, vol. 50.
Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.
Shigemoto, et al., Differential Presynaptic Localization of Metabotropic Glutamate Receptor Subtypes in the Rat Hippocampus, The Journal of Neuroscience, Oct. 1, 1997, pp. 7503-7522, vol. 17 Issue 19, Society for Neuroscience.
Suzuki, et al., Rapid Coupling of Methyl Iodide with Aryltributylstannanes Mediated by Palladium(0) Complexes: A General Protocal for the Synthesis of CH3-Labeled PET Tracers., Chem. Eur. J., 1997, pp. 2039-2042, vol. 3 Issue 12.
V. Craig Jordan, "Tamoxifen: A Most Unlikely Pioneering Medicine", Nature Reviews Drug Discovery, 2003, pp. 205-213, vol. 2.
Vippagunta et al, Crystalline solids, Advanced Drug Delivery Reviews, May 16, 2001, pp. 3-26, vol. 48 No. 1.
International Search Report for PCT/EP2016/081542 dated Mar. 13, 2017.
Bell et al., "DSM-IV: Diagnostic and Statistical Manual of Mental Disorders," JAMA, vol. 272, No. 10, Sep. 1994, pp. 828-829.
Higgins et al., "Pharmacological manipulation of mGlu2 receptors influences cognitive performance in rodents", Neuropharmacology, vol. 46, May 2004, pp. 907-917.
Hoffmann-La Roche, ClinicalTrials.gov Identifier NCT01457677, Feb. 2014, 3 sheets.
Int. search report for PCT/EP2014/061478, dated Aug. 2014, 4 sheets.
Int. search report for PCT/EP2015/067530, dated Nov. 2015, 3 sheets.
Int. search report for PCT/EP2015/067533, dated Oct. 2015, 3 sheets.
Int. search report for PCT/EP2015/067534, dated Sep. 2015, 3 sheets.
Int. search report for PCT/EP2015/067538, dated Sep. 2015, 4 sheets.
Int. search report for PCT/EP2015/067572, dated Sep. 2015, 4 sheets.
Int. search report for PCT/EP2015/078296, dated Feb. 2016, 5 sheets.
Int. search report for PCT/EP2015/079216, dated Feb. 2016, 5 sheets.
Int. search report for PCT/EP2015/078285, dated Feb. 2016, 4 sheets.
Int. search report for PCT/EP2015/078285 , dated Mar. 2017, 5 sheets.
Sheffler et al., "Recent Progress in the Synthesis and Characterization of Group II Metabotropic Glutamate Receptor Allosteric Modulators", ACS Chemical Neuroscience, vol. 2, Apr. 2011, pp. 382-393.

* cited by examiner

RADIOLABELLED MGLUR2/3 PET LIGANDS

This application is a 371 National Stage Application of International Application No. PCT/EP2016/081542 with an international filing date of Dec. 16, 2016 and claims the benefit of priority to European Application No. EP15201240.7 filed Dec. 18, 2015, the entire disclosures of each of which are hereby incorporated in their entirety.

FIELD OF THE INVENTION

The present invention relates to novel, radiolabelled mGluR2/3 ligands, selective versus other mGlu receptors, which are useful for imaging and quantifying the metabotropic glutamate receptors mGlu2 and 3 in tissues, using positron-emission tomography (PET). The invention is also directed to compositions comprising such compounds, to processes for preparing such compounds and compositions, to the use of such compounds and compositions for imaging a tissue, cells or a mammal, in vitro or in vivo and to precursors of said compounds.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer's disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain therapeutics) describes 4H-pyrazolo[1,5-a]quinazolin-5-ones and 4H-pyrrolo[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD). WO2014195311 (Janssen Pharmaceutica NV) discloses 6,7-dihydropyrazolo[1,5-a]pyrazine-4(5H)-one compounds and their use as mGluR2 NAMs.

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides such as, for example, $^{15}O$, $^{13}N$, $^{11}C$ and $^{18}F$ for detection. Several positron emission tomography radiotracers have been reported so far for in vivo imaging of mGluRs. There is still a need to provide improved positron emission tomography radiotracers for imaging Group II mGlu receptors.

SUMMARY OF THE INVENTION

The present invention relates to a compound having the Formula (I)

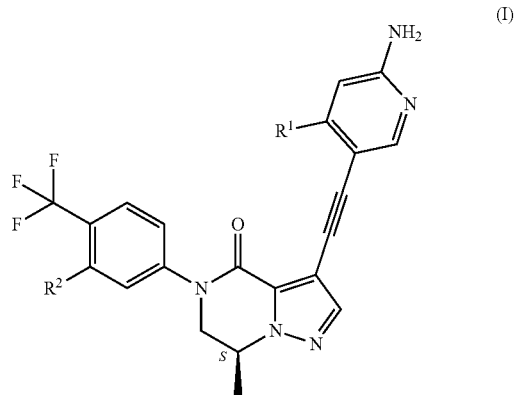

wherein $R^1$ is —$CH_2F$ and $R^2$ is —H, or $R^1$ is —H and $R^2$ is —$CH_2F$, and wherein at least one atom is radiactive, or a pharmaceutically acceptable salt or a solvate thereof.

In a particular embodiment, the compound of Formula (I) is compound 1

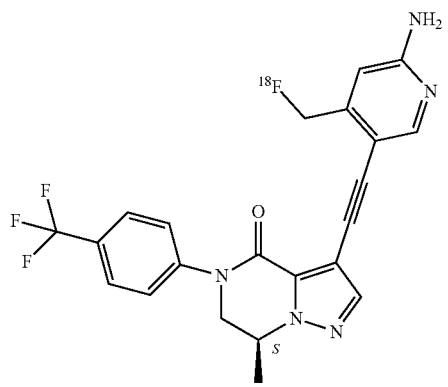

compound 1 or a pharmaceutically acceptable salt or a solvate thereof.

In a particular embodiment, the compound of Formula (I) is compound 2

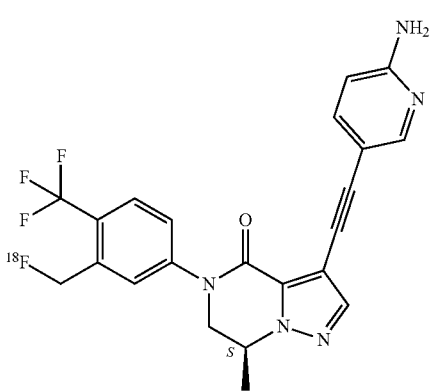

compound 2 or a pharmaceutically acceptable salt or a solvate thereof.

The invention also relates to precursor compounds for the synthesis of compound 1.

Thus, the present invention also relates to compounds of Formulae P-1 and P-2

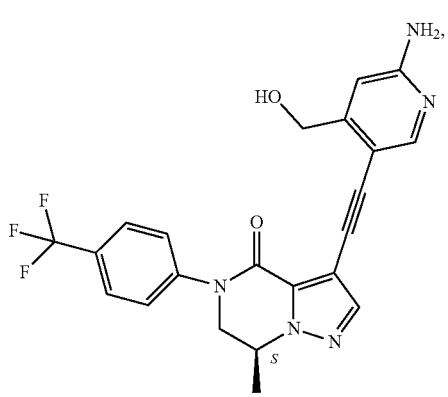

P-1

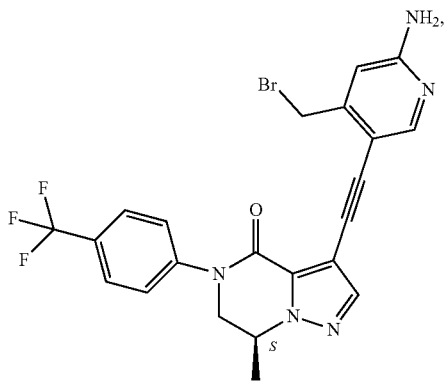

P-2 and the pharmaceutically acceptable salts and the solvates thereof.

The invention also relates to precursor compounds for the synthesis of compound 2. Thus, the present invention also relates to compounds of Formulae P-3 and P-4

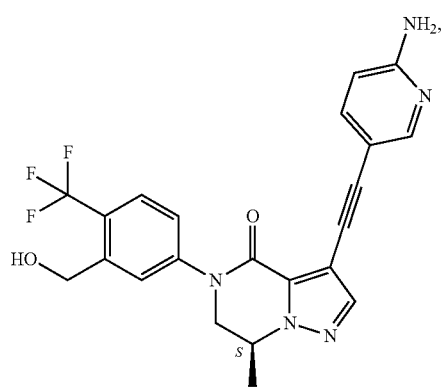

P-3

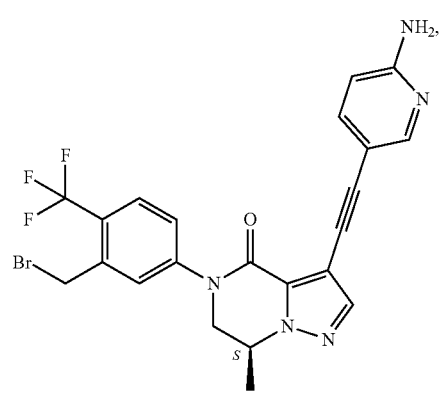

P-4 and the pharmaceutically acceptable salts and the solvates thereof.

The invention also relates to a pharmaceutical composition comprising a compound of Formula (I) or a pharmaceutically acceptable salt thereof and a pharmaceutically acceptable carrier or diluent. In a particular embodiment, said pharmaceutical composition is particularly suitable for diagnosis and may be referred to therefore as a diagnostic pharmaceutical composition. In particular, said pharmaceutical composition is a sterile solution. Thus, illustrative of the invention is a sterile solution comprising a compound of Formula (I) described herein.

The invention further relates to the use of a compound of Formula (I) as an imaging agent. Therefore, exemplifying the invention is a use of a compound of Formula (I) as described herein, for, or a method of, imaging a tissue, cells or a mammal, in vitro or in vivo. In particular, the invention relates to a compound of Formula (I) as described herein, for use as a contrast agent for imaging a tissue, cells or a mammal, in vitro, ex vivo, or in vivo. The invention further relates to a composition comprising a compound of Formula (I) for use as a contrast agent for imaging a tissue, cells or a mammal, in vitro, ex vivo, or in vivo.

The invention also relates to a method for imaging a tissue, cells or a mammal, comprising contacting with or providing or administering a detectable amount of a labelled compound of Formula (I) as described herein to a tissue, cells or a mammal, and detecting the compound of Formula (I).

Further exemplifying the invention is a method of imaging a tissue, cells or a mammal, comprising contacting with or providing or administering to a tissue, cells or a mammal, a compound of Formula (I) as described herein, and imaging the tissue, cells or mammal with a positron-emission tomography imaging system. Additionally, the invention refers to a process for the preparation of a compound according to Formula (I) as described herein, comprising (a) the steps of (a-1) reacting a compound of Formula (P-1) with methanesulfonic anhydride in the presence of a base and an inert solvent, for example, trimethylamine or triethylamine and dichloromethane, and (a-2) reacting the compound obtained in step (a-1) with a nucleophilic radioactive fluorinating reagent [$^{18}$F]F$^-$ in the presence of a base in an inert solvent or (b) the step of reacting a compound of Formula (P-2) with a nucleophilic radioactive fluorinating reagent [$^{18}$F]F$^-$ in the presence of a base in an inert solvent or (c) the steps of (c-1) reacting a compound of Formula (P-3) with methanesulfonic anhydride in the presence of a base and an inert solvent, for example, trimethylamine or triethylamine and dichloromethane, and (c-2) reacting the compound obtained in step (c-1) with a nucleophilic radioactive fluorinating reagent [$^{18}$F]F$^-$ in the presence of a base in an inert solvent

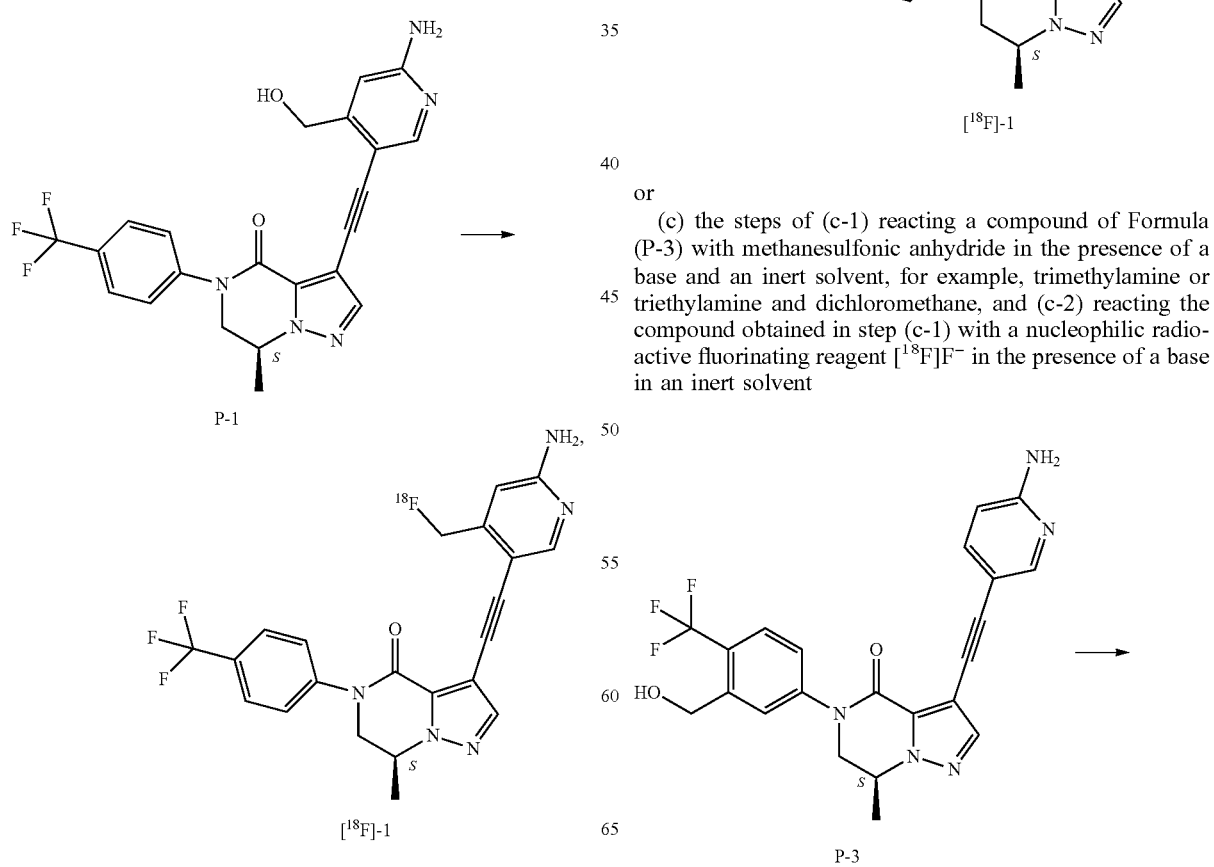

7
-continued

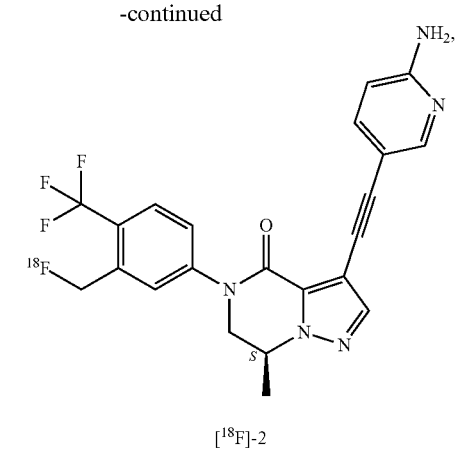

[¹⁸F]-2 or (d) the step of reacting a compound of Formula (P-4) with a nucleophilic radioactive fluorinating reagent [¹⁸F]F⁻ in the presence of a base in an inert solvent

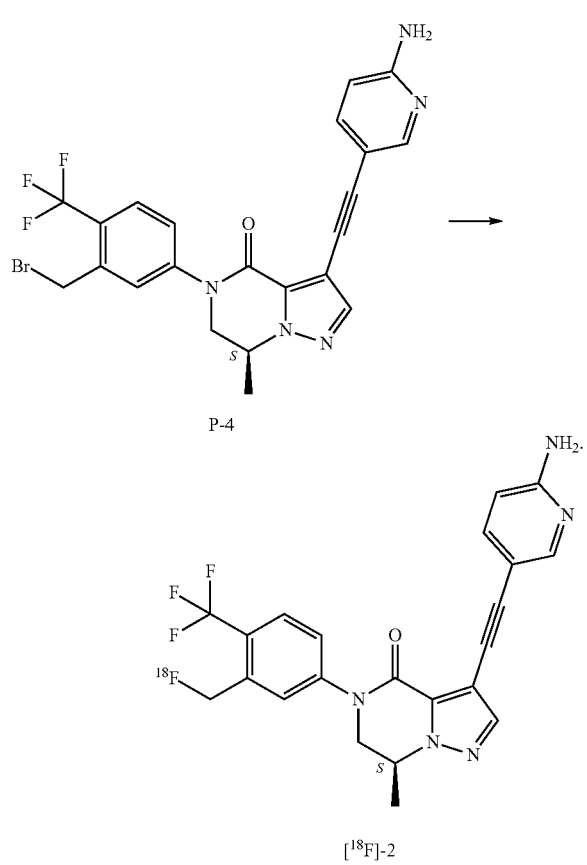

Suitable nucleophilic radioactive fluorinating reagents in steps (a-2), (b), (c-2) and (d) are, for instance, K[¹⁸F]/Kryptofix 222 or tetraalkylammonium salts incorporating radioactive fluoride [¹⁸F]F⁻. Suitable bases in steps (a-2), (b), (c-2) and (d), are, for instance $K_2CO_3$ or $Cs_2CO_3$. Suitable solvents in steps (a-2), (b), (c-2) and (d), are, for instance, DMSO, $CH_3CN$ or DMF, optionally with the addition of a small amount of water.

8

DESCRIPTION OF THE FIGURES

In FIGS. 2 and 4 the following legend is used:
—◆— Pons Baseline  —□— Cerebellum baseline  —▲— Frontal baseline  —✳— Hippocampus baseline  —✳— Striatum baseline  —○— Pons blocked  —+— cerebellum blocked  —✱— Striatum blocked  —✳— Hippocampus 1  —▲— Emetal blocked

DETAILED DESCRIPTION OF THE INVENTION

Figure 1A:
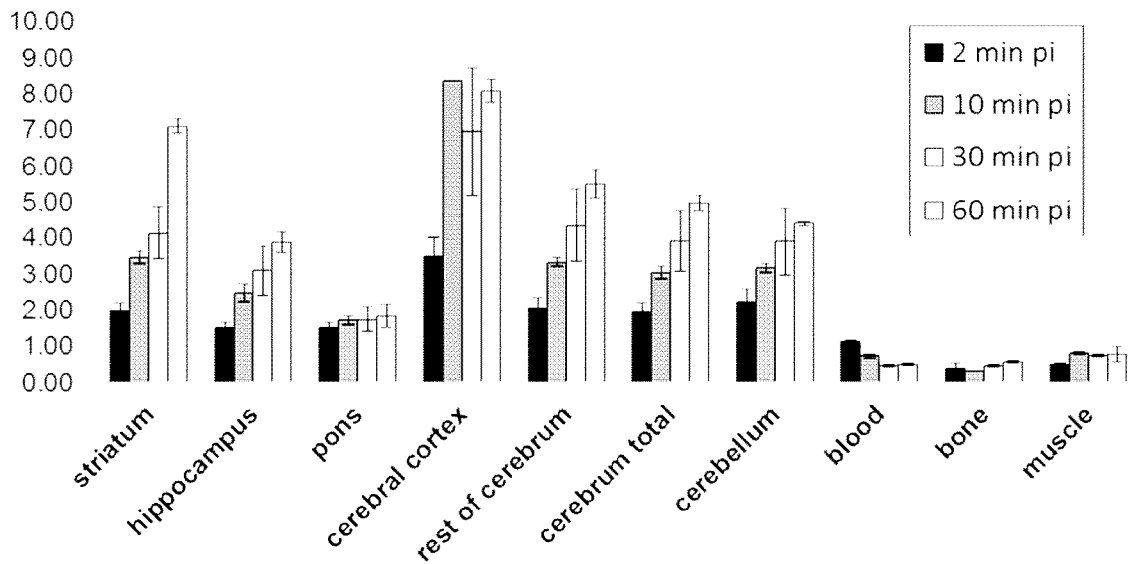
FIG. 1a shows the biodistribution of [¹⁸F]-1 in brain areas in SD rats.
Figure 1B:
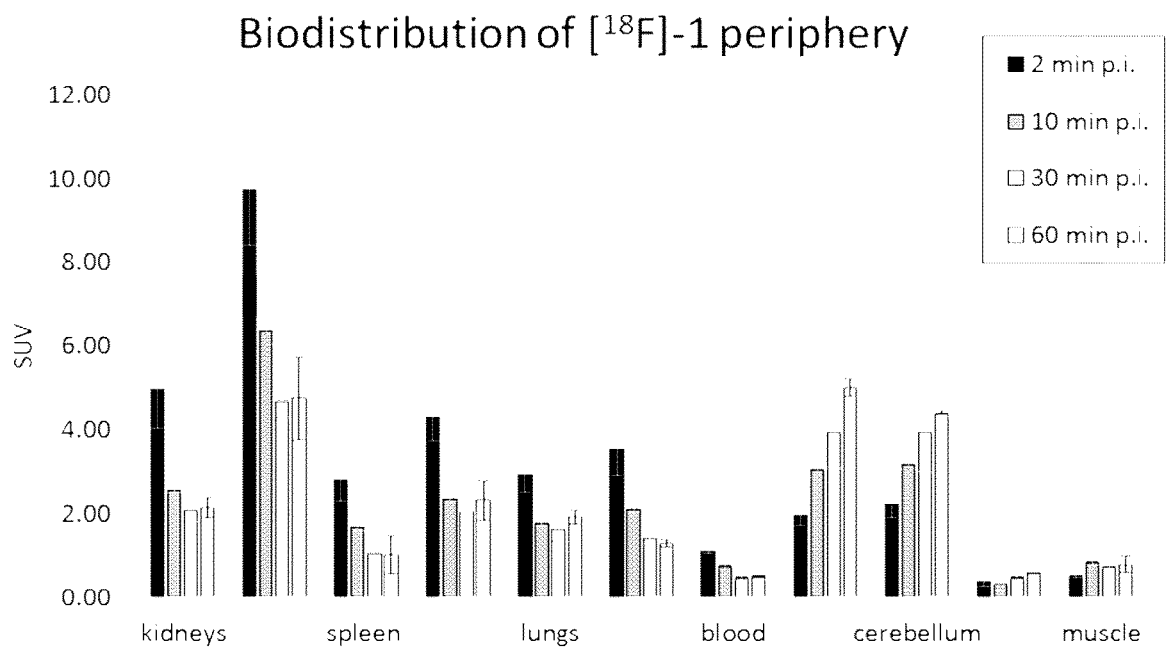
FIG. 1b shows the biodistribution of [¹⁸F]-1 in periphery in SD rats.
Figure 2:
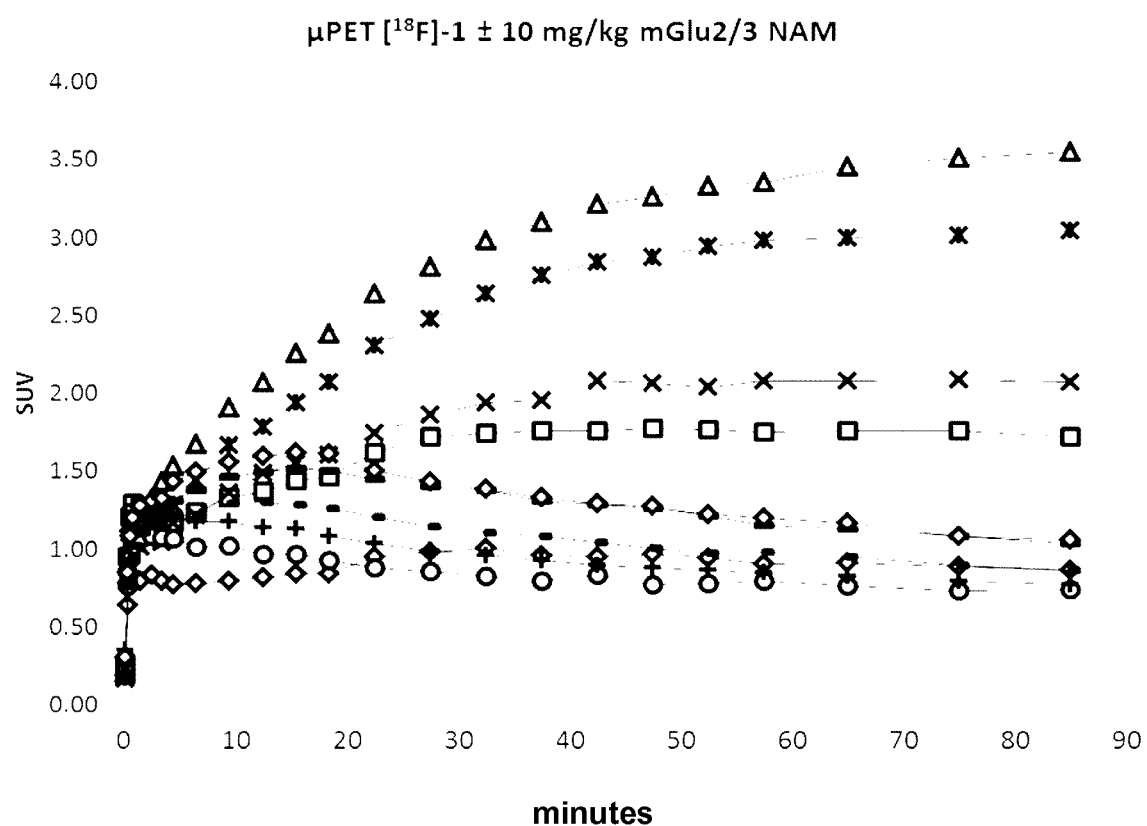
FIG. 2 shows the time activity curves for the uptake of [¹⁸F]-1 with and without treatment of compound A (a NAM compound, selective for mGlu2/3 (~20 fold selective for 2 over 3) vs other mGluRs), indicated in the figure as mGlu2/3 NAM in SD rats.
Figure 3A:
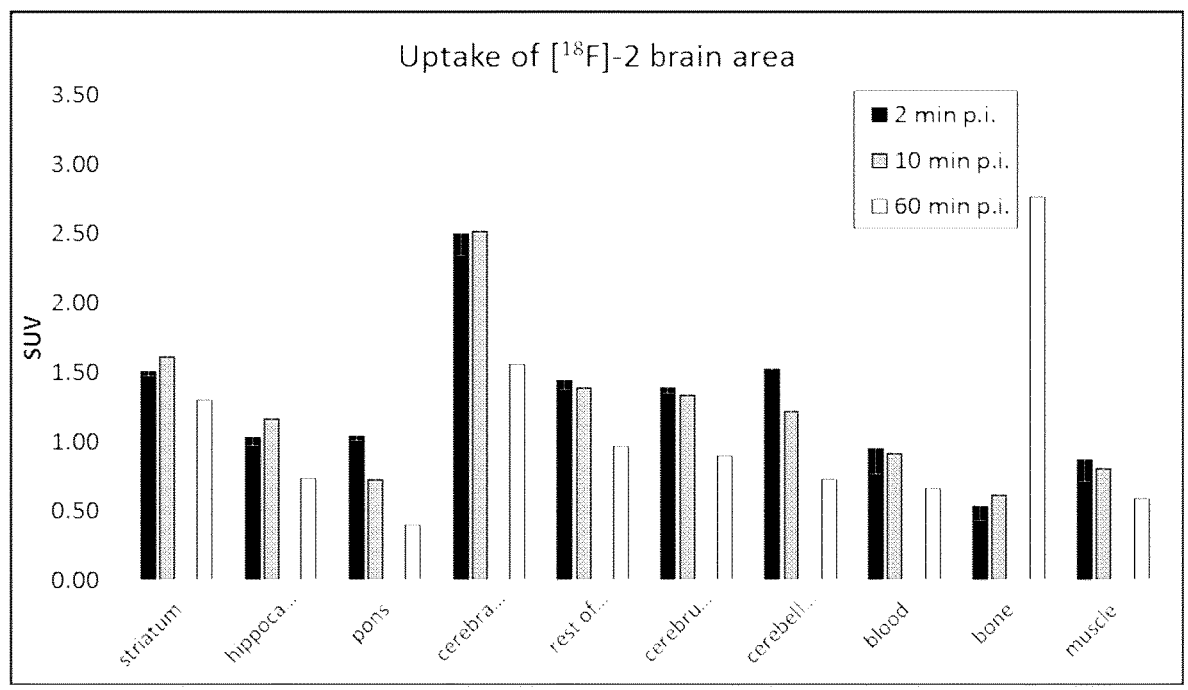
FIG. 3a shows the biodistribution of [¹⁸F]-2 in brain areas in SD rats.
Figure 3B:
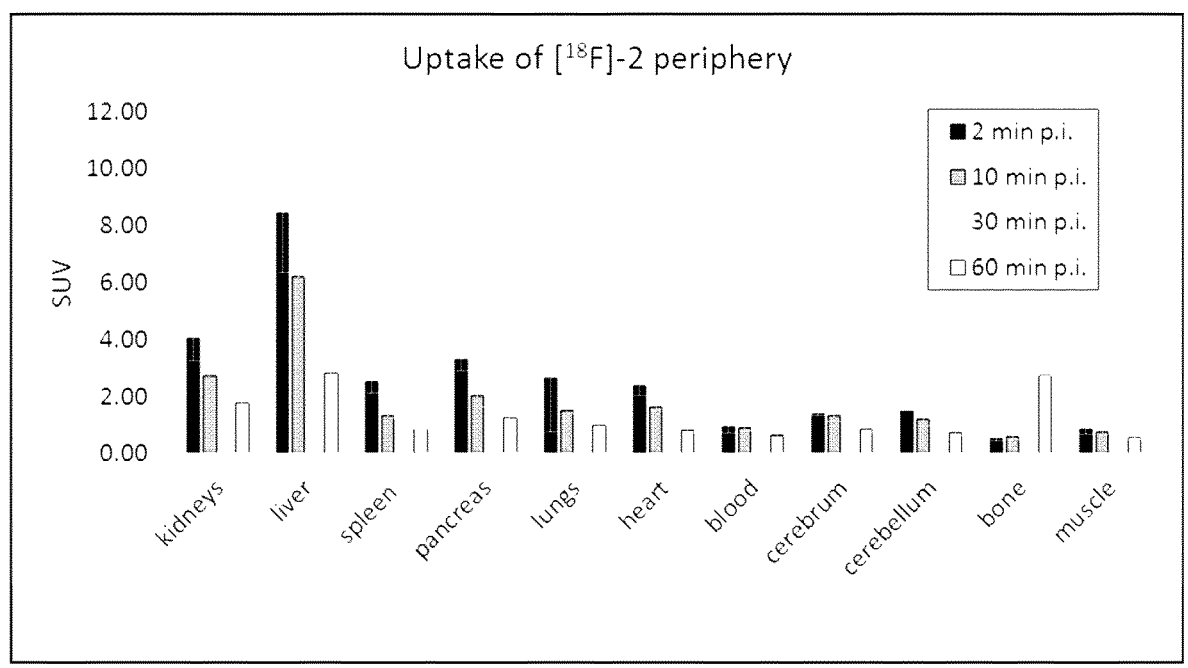
FIG. 3b shows the biodistribution of [¹⁸F]-2 in periphery in SD rats.

As already mentioned, the compounds of Formula (I) and compositions comprising the compounds of Formula (I) can be used for imaging a tissue, cells or a mammal, in vitro or in vivo. In particular, the invention relates to a method of imaging or quantifying the mGluR2/3 receptors in a tissue, cells or a mammal in vitro or in vivo.

The cells and tissues are preferably central nervous system cells and tissues in which the mGluR2/3 receptors are abundant. As already mentioned, the mGluR2/3 receptors are abundant in central nervous system tissue, more in particular, in central nervous system tissue forming the brain; more in particular, forming the cerebral cortex, thalamic regions, accessory olfactory bulb, hippocampus, amygdala, caudate-putamen and nucleus accumbens.

When the method is performed in vivo, the compound of Formula (I) can be administered intravenously, for example, by injection with a syringe or by means of a peripheral intravenous line, such as a short catheter.

When the mammal is a human, the compound of Formula (I) or a sterile solution comprising a compound of Formula (I), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (I), as defined herein, or a composition comprising a compound of Formula (I) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (I), as defined herein, or a sterile formulation comprising a compound of Formula (I) to the human, and imaging the tissue or cells with a positron-emission tomography imaging system.

In a further embodiment, the invention relates to a method of imaging or quantifying the mGluR2/3 receptors in a mammal, comprising the intravenous administration of a compound of Formula (I), or a composition comprising a compound of Formula (I) to the mammal, and imaging with a positron-emission tomography imaging system.

In another embodiment, the invention relates to the use of a compound of Formula (I) for imaging a tissue, cells or a mammal, in vitro or in vivo, or the invention relates to a compound of Formula (I), for use in imaging a tissue, cells or a mammal in vitro or in vivo, using positron-emission tomography.

The invention also relates to a method for imaging or quantifying the mGlu2 and 3 receptors in a mammal, the method comprising providing a detectable amount of a compound of Formula (I) to a mammal and detecting the compound of Formula (I) associated with mGlu2 and 3 receptors. The method also allows for determining mGlu2 and 3 receptor occupancy by other non-radiolabelled compounds, therefore, the invention relates to the compound of Formula (I) as defined herein, or the pharmaceutical composition according to the invention, for use in determining mGlu2 and 3 receptor site occupancy by other non-radiolabelled compounds.

Furthermore, the invention relates to a method of assessing a disorder or predisposition thereto related to the mGlu2 and 3 receptors in a subject, the method comprising providing a detectable amount of a compound of Formula (I) or pharmaceutical composition according to the invention, wherein the compound of Formula (I) passes the blood-brain barrier and preferentially binds to mGlu2 and 3 receptors in brain tissue, allowing the compound to distribute into the brain tissue, and imaging the brain tissue.

The compound is provided to a subject in a detectable amount and after sufficient time has passed for the compound to become associated with the mGlu2 and 3 receptors, the labelled compound is detected noninvasively.

Definitions

As used herein, the term "composition" is intended to encompass a product comprising the specified ingredients in the specified amounts, as well as any product which results, directly or indirectly, from combinations of the specified ingredients in the specified amounts.

The term "detectable amount" refers to the concentration of compound above the lowest limit of detection of the imaging instrument, in particular, of the PET scanning instrument.

The absolute configuration is specified according to the Cahn-Ingold-Prelog system.

Addition salts of the compounds according to the invention also intended to be encompassed within the scope of this invention.

Acceptable salts of the compounds of the invention are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention. The pharmaceutically acceptable salts are defined to comprise the therapeutically active non-toxic acid addition salt forms that the compounds according to the invention are able to form. Said salts can be obtained by treating the base form of the compounds according to the invention with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzensulfonic acid, p-toluenesulfonic acid, cyclamic acid, salicylic acid, p-aminosalicylic acid and pamoic acid.

Conversely, said salt forms can be converted into the free base form by treatment with an appropriate base.

In addition, some of the compounds of the present invention may form solvates with water (i.e., hydrates) or common organic solvents, and such solvates are also intended to be encompassed within the scope of this invention.

The term "subject" as used herein, refers to an animal, preferably a mammal, most preferably a human, who is or has been the object of treatment, observation or experiment. Unless otherwise stated, "subject" includes both, healthy animals and animals afflicted by different diseases or disorders.

The term "mammal" refers, in particular to humans, mice, dogs and rats.

The term "cell" refers to a cell expressing or incorporating the mGlu2 and/or 3 receptor.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006).

Applications

The compounds according to the present invention find various applications for imaging tissues, cells or a mammal, both in vitro and in vivo. Thus, for instance, they can be used to map the differential distribution of mGluR2/3 in subjects of different age and sex. Further, they allow one to explore for differential distribution of mGluR2/3 in subjects afflicted by different diseases or disorders. Thus, abnormal distribution may be helpful in diagnosis, case finding, stratification of subject populations, and in monitoring disease progression in individual subjects. The radioligands may further find utility in determining mGluR2/3 site occupancy by other ligands. Since the radioligand is administered in trace amounts, i.e. in detectable amounts for example for PET imaging, no therapeutic effect may be attributed to the administration of the radioligands according to the invention.

Experimental Part

General

As used herein, the term "aq." means aqueous, "DCM" means dichloromethane, "DIPE" means diisopropyl ether, "DMF" means N,N-dimethylformamide, "DMSO" means dimethyl sulfoxide, "DSC" means differential scanning calorimetry, "Et$_3$N/TEA" means triethylamine, "EtOH" means ethanol, "EtOAc" means ethyl acetate, "h" means hours, "HPLC" means high-performance liquid chromatography, "LCMS" means liquid chromatography/mass spectrometry, "iPrOH" means isopropyl alcohol, "MeOH" means methanol, "[M+H]$^+$" means the protonated mass of the free base of the compound, "min" means minutes, "m.p." means melting point, "PdCl$_2$(PPh$_3$)$_2$" means bis(triphenylphosphine)palladium(II) chloride and PPh$_3$ means triphenylphosphine, "RP" means reverse phase, "r.t./RT" means room temperature" "R$_t$" means retention time (in minutes), "sat." means saturated, "sol." means solution, "XtalFluor-E®" means (diethylamino)difluorosulfonium tetrafluoroborate.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

Several methods for preparing the compounds of this invention are illustrated in the following examples, which are intended to illustrate but not to limit the scope of the present invention. Unless otherwise noted, all starting materials were obtained from commercial suppliers and used without further purification.

PREPARATION OF INTERMEDIATE COMPOUNDS

Intermediate 1 (I-1)

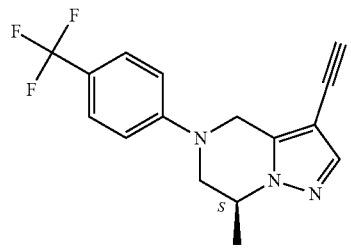

K$_2$CO$_3$ (171 mg, 1.24 mmol) was added to a stirred solution of (7S)-6,7-dihydro-3-iodo-7-methyl-5-[4-(trifluoromethyl)phenyl]-pyrazolo[1,5-a]pyrazin-4(5H)-one ([1639901-88-4], WO 2014195311, 0.97 g, 2.48 mmol) in MeOH (10 mL) at r.t. and under nitrogen. The mixture was stirred at rt for 2 h. The solvent was removed in vacuo and the residue was diluted with water and extracted with EtOAc. The organic layer was separated, dried (Na$_2$SO$_4$), filtered and the solvents evaporated in vacuo. The crude product was purified by flash column chromatography (silica; EtOAc in DCM 0/100 to 30/70). The desired fractions were collected and the solvents evaporated in vacuo to yield intermediate compound I-1 as a beige solid (549 mg, 69%).

Intermediate 2 (I-2)

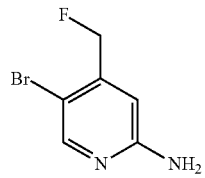

Xtalfluor-E® (0.338 g; 1.478 mmol) and trimethylamine trihydrofluoride (0.241 mL; 1.478 mmol) were added to a stirred mixture of 2-amino-5-bromo-4-pyridinemethanol (0.2 g; 0.985 mmol) in DCM (14 mL) in a sealed tube at 0° C. and under nitrogen. The mixture was allowed to warm and stirred for 18 h. The mixture was carefully treated with sat. NaHCO$_3$/brine at 0° C. and extracted with DCM. The organic layer was separated, dried (Na$_2$SO$_4$), filtered and evaporated in vacuo. The residue was purified by flash column chromatography (silica; ethyl acetate in DCM 0/100 to 30/70). The desired fractions were collected and concentrated in vacuo to yield intermediate compound I-2 (94.4 mg; 47%) as a beige solid.

Intermediate 3 (I-3)

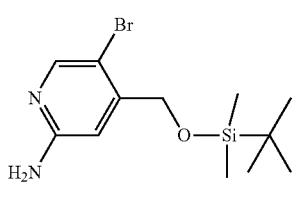 [SMILES: CC(C)(C)[Si](C)(C)OCc1cc(N)ncc1Br]

Imidazole (0.41 g, 5.89 mmol) was added to a mixture of 2-amino-5-bromo-4-(hydroxymethyl)pyridine (0.797 g, 3.93 mmol) and tert-butyldimethylsilyl chloride (0.89 g, 5.89 mmol) in DMF (7.9 mL) at r.t. The mixture was stirred at r.t. for 16 h. The mixture was treated with sat. NaHCO$_3$ at 0° C. and extracted with EtOAc. The organic layer was separated, washed with brine, dried (Na$_2$SO$_4$), filtered and evaporated in vacuo. The crude product was purified by flash column chromatography (silica; EtOAc/DCM 0/100 to 50/50). The desired fractions were collected and evaporated in vacuo to yield I-3 (0.34 g, 67%) as a white solid.

Intermediate 4 (I-4)

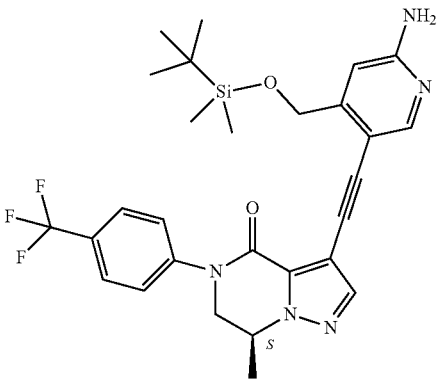

Copper(I) iodide (3.20 mg, 0.0017 mmol) was added to a deoxygenated stirred mixture of I-1 (0.54 g, 1.68 mmol), I-3 (0.64 g, 2.02 mmol), TEA (0.70 mL), PdCl$_2$(PPh$_3$)$_2$ (23.61 mg, 0.034 mmol) and PPh$_3$ (8.82 mg, 0.034 mmol) in DMF (11 mL) under nitrogen. The mixture was stirred at 70° C. for 18 h. The mixture was diluted with NH$_4$OH/brine and extracted with EtOAc. The organic layer was separated, dried (Na$_2$SO$_4$), filtered and the solvents evaporated in vacuo. The residue was purified by flash column chromatography (silica; EtOAc/DCM 0/100 to 100/0). The desired fractions were collected and concentrated in vacuo to yield I-4 (0.53 g, 57%) as a pale brown solid.

Intermediate 5 (I-5)

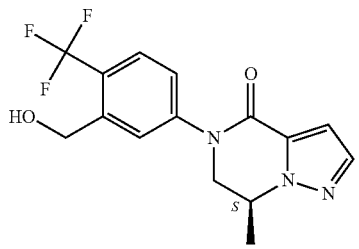

Copper(I) iodide (860.27 mg, 4.52 mmol) was added to a stirred suspension of (7S)-6,7-dihydro-7-methyl-pyrazolo[1,5-a]pyrazin-4(5H)-one ([1639901-79-3, WO2014195311, 2.05 g, 13.55 mmol), 5-bromo-2-(trifluoromethyl)benzyl alcohol (2.88 g, 11.29 mmol), $K_2CO_3$ (3.12 g, 22.59 mmol) and N,N-dimethylethylenediamine (571.3 µL, 4.52 mmol) in toluene (15 mL) in a sealed tube and under nitrogen. The mixture was stirred at 105° C. for 18 h. Then the mixture was diluted with water and $NH_3$ 32% and extracted with DCM. The organic layer was separated, dried ($Na_2SO_4$), filtered and the solvents evaporated in vacuo. The crude product was purified by flash column chromatography (silica; EtOAc/heptane 40/60 to 70/30). The desired fractions were collected and concentrated in vacuo to yield I-5 (3.24 g, 88%) as a white solid.

Intermediate 6 (I-6)

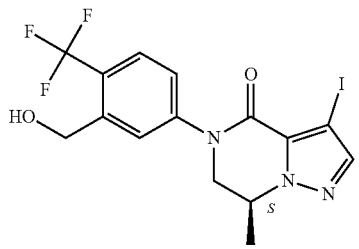

Iodine (1.75 g, 6.91 mmol) was added to a solution of I-5 (3.21 g, 9.87 mmol) and ammonium cerium(IV) nitrate (3.79 g, 6.91 mmol) in $CH_3CN$ (46 mL) and the mixture was stirred at 75° C. for 45 min. Then the mixture was cooled to r.t., diluted with EtOAc and washed with diluted $Na_2S_2O_3$. The organic layer was separated, dried ($Na_2SO_4$), filtered and the solvents evaporated in vacuo. The crude product was purified by flash column chromatography (silica; EtOAc/heptane 20/80 to 40/60). The desired fractions were collected and evaporated in vacuo to give I-6 (4.1 g, 92%) as a white foam.

Preparation of P-1

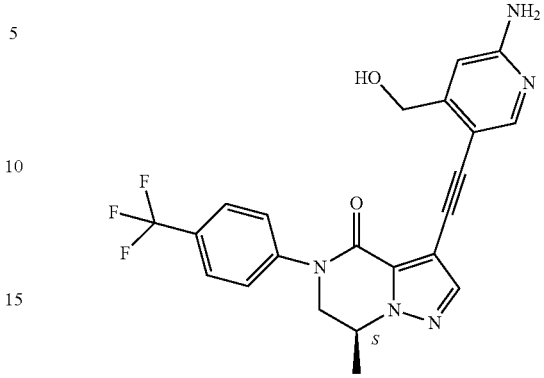

HCl (6M in iPrOH, 5.07 mL, 30.43 mmol) was added to a solution of I-4 (0.533 g, 0/96 mmol) in EtOH (111 mL) at r.t. and the r.m. was stirred for 18 h. The mixture was then evaporated in vacuo. The residue was treated with $NH_4OH$ and extracted with EtOAc.

The organic layer was separated, dried ($Na_2SO_4$), filtered and evaporated in vacuo. The residue was purified by flash column chromatography (silica; EtOAc/DCM 0/100 to 100/0). The desired fractions were collected and evaporated in vacuo. Then the product was triturated with $Et_2O$, filtered and dried to yield P-1 (0.23 g, 54%) as a beige solid.

Preparation OF P-2

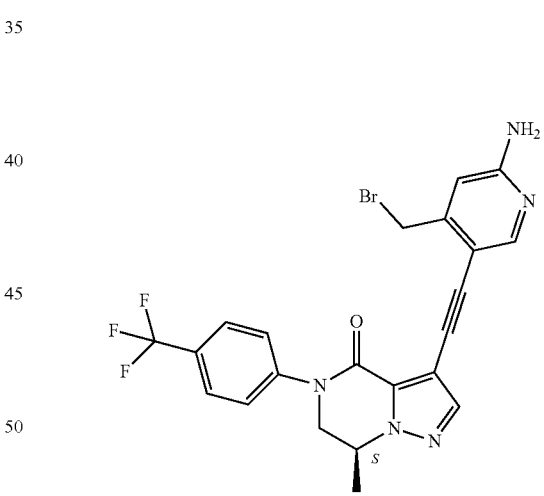

Polymer supported triphenylphosphine (0.24 g, 0.52 mmol) was added to a mixture of P-1 (45.5 mg, 0.10 mmol) and carbon tetrabromide (0.17 g, 0.52 mmol) in DCM (12. mL) at 0° C. under $N_2$ atmosphere. The mixture was stirred at r.t. for 18 h, then treated with DCM and filtered, then the polymeric resin was washed with MeOH and DCM several times. The filtrate was diluted with heptane and evaporated in vacuo at r.t. to yield P-2 as a brown syrup that was used without further purification.

Preparation of P-3

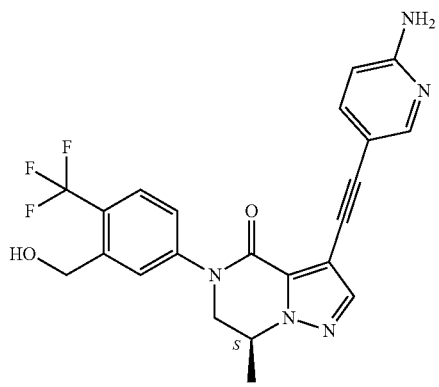

Copper (I) iodide (4.22 mg, 0.022 mmol) was added to a stirred mixture of I-6 (1 g, 2.22 mmol), 5-ethynyl-2-pyridinamine (523.68 mg, 4.43 mmol), TEA (924.23 µL, 6.65 mmol), PdCl$_2$(PPh$_3$)$_2$ (31.11 mg, 0.044 mmol) and PPh$_3$ (11.63 mg, 0.044 mmol) in DMF (10 mL). The mixture was purged with N$_2$ for 5 min and then it was stirred at 90° C. for 5 h. The residue was diluted with water and extracted with EtOAc. The organic layer was separated, dried (Na$_2$SO$_4$), filtered and concentrated in vacuo. The crude product was purified by flash column chromatography (silica; MeOH/DCM 0/100 to 05/95). The desired fractions were collected and concentrated in vacuo to yield P-3 (923 mg, 92%).

Preparation of P-4

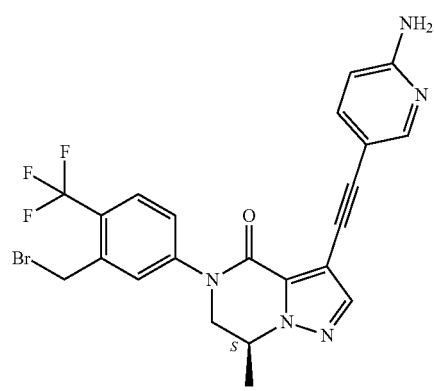

To a stirred solution of P-3 (200 mg, 0.45 mmol) in DCM (16 mL) was added phosphorus tribromide (1 M in DCM, 679.64 µL, 0.68 mmol), turning the yellow solution into a white suspension. The reaction was stirred at r.t. for 30 min, dissolving the white suspension progressively. Afterwards, the reaction was diluted with DCM/heptane (final 1/1 ratio) and washed with a sat. aq. sol. NaHCO$_3$. The organic layer was separated, dried (MgSO$_4$), filtered and the solvents evaporated in vacuo at r.t. (N.B. product reacts itself upon concentration) to give P-4 (143 mg, 63%).

Preparation of Compound [$^{19}$F]-1

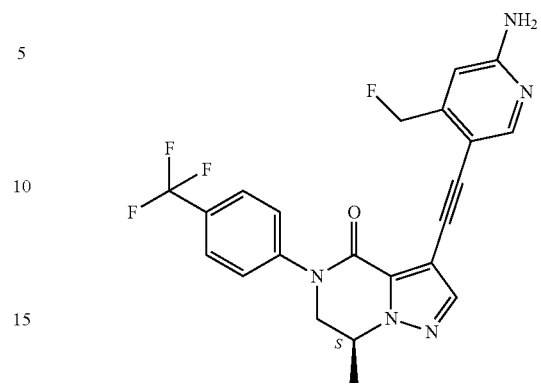

Copper (I) iodide (0.88 mg, 0.005 mmol) was added to a deoxygenated stirred mixture of I-1 (147.0 mg, 0.46 mmol), I-2 (94.4 mg, 0.46 mmol), TEA (192 µL, 1.38 mmol), PdCl$_2$(PPh$_3$)$_2$ (6.46 mg, 0.009 mmol) and PPh$_3$ (2.42 mg, 0.009 mmol) in DMF (6.7 mL) under nitrogen. The mixture was stirred at 70° C. for 2 days. The mixture was diluted with NH$_4$OH/water and extracted with EtOAc. The organic layer was separated, dried (Na$_2$SO$_4$), filtered and the solvents evaporated in vacuo. The residue was purified by flash column chromatography (silica; EtOAc/DCM 0/100 to 87/13). The desired fractions were collected and evaporated in vacuo to yield a fraction with pure compound. A mixed fraction was dissolved in Et$_2$O with some drops of 2-propanol and it was converted into the hydrochloric acid salt by treating with HCl/2-propanol. The solid salt was filtered, washed with Et$_2$O and dried, then it was treated with water/32% NH$_4$OH until basic pH and extracted with EtOAc. The organic layer was separated, dried (Na$_2$SO$_4$), filtered and evaporated in vacuo to yield another fraction of pure compound. The two fractions with pure compound were combined, triturated with Et$_2$O/DIPE, filtered and dried to yield compound [$^{19}$F]-1 (32.7 mg, 16%) as a beige solid.

Preparation of Compound [$^{19}$F]-2

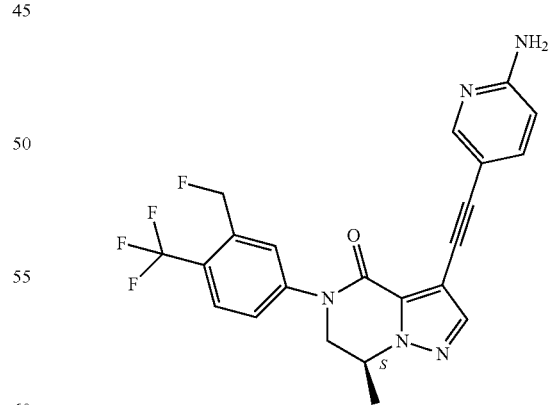

Bis(2-methoxyethyl)amino-sulfur trifluoride (0.915 mL, 4.961 mmol) was added to a stirred solution of compound P-3 (438 mg, 0.992 mmol) in DCM (6.2 mL) at 0° C. and under nitrogen. The mixture was stirred at 0° C. for 45 min. Then the mixture was treated with sat. sol. NaHCO$_3$ at 0° C. and extracted with DCM and EtOAc. The organic layer was separated, dried ($Na_2SO_4$), filtered and the solvents concentrated in vacuo. The crude product was purified by flash column chromatography (silica; EtOAc in DCM 0/100 to 50/50). The desired fractions were collected and the solvents concentrated in vacuo. The residue was triturated with $Et_2O$ to yield an impure fraction as a yellow solid and was purified by RP HPLC (Stationary phase: C18 XBridge 50×100 5 μm, Mobile phase: Gradient from 80% 10 mM $NH_4CO_3H$ pH 9 solution in Water, 20% $CH_3CN$ to 0% 10 mM $NH_4CO_3H$ pH 9 solution in Water, 100% $CH_3CN$) to yield compound [$^{19}F$]-2 (55 mg, 12%) as a pale yellow solid. $^1H$ NMR (400 MHz, $CDCl_3$) δ ppm 1.71 (d, J=6.5 Hz, 3H) 3.99 (dd, J=12.7, 7.4 Hz, 1H) 4.26 (dd, J=12.5, 4.2 Hz, 1H) 4.59 (br. s, 2H) 4.74 (quind, J=6.7, 4.4 Hz, 1H) 5.63 (d, J=46.7 Hz, 2H) 6.43 (dd, J=8.6, 0.7 Hz, 1H) 7.52 (dd, J=8.4, 0.8 Hz, 1H) 7.57 (dd, J=8.6, 2.3 Hz, 1H) 7.67 (s, 1H) 7.72-7.76 (m, 2H) 8.27 (dd, J=2.2, 0.6 Hz, 1H).

Preparation of Compounds [$^{18}F$]-1 AND [$^{18}F$]-2

General

Chemicals were obtained from Sigma-Aldrich (Saint Louis, USA) and were used without further purification. [$^{18}F$]$F^-$ was produced by an IBA Cyclone 18/9 cyclotron (Louvain-la-Neuve, Belgium).

Preparative HPLC was performed on an Xbridge C18 column (4.6×250 mm, 5 μm; Waters, Milford USA), using EtOH/0.01 M phosphate buffer in water pH 7.4 (39/61 v/v) at flow rate 1 mL·$min^{-1}$ and wavelength of 254 nm (method A).

The identity of the radiotracers was confirmed using the same analytical HPLC methods as described above after co-injection with their non-radioactive analogue.

Millex GV filters were obtained from Millipore (Amsterdam, The Netherlands). Radioactivity was counted using the Wizard 1480 automated gamma counter (Perkin Elmer, Waltham, USA).

For [$^{18}F$]-1 and [$^{18}F$]-2, the corresponding alcohol precursors P1 and P-3, respectively, were mesylated immediately prior to radiosynthesis according to the following protocol:

P-1 or P-3 (~7.5 mg, 1 eq) was dissolved in DCM (2 mL), then trimethylamine (2.5 μL, 1.1 eq) was added, followed by the addition of methanesulfonic anhydride (3.5 mg, 1.1 eq) and the mixture was incubated for 60 min at r.t. Then the r.m. was washed with water (2×) and dried over $MgSO_4$, filtered and evaporated to dryness at 30° C. in vacuo. Hereafter the product was azeotropically dried using $CH_3CN$ (3×2 mL) also at 30° C. in vacuo. After evaporation of the last portion of $CH_3CN$, the mesylated precursor was ready for use. TLC (silica plates eluted with 95% DCM and 5% MeOH) was used to check the purity of the corresponding precursor.

[$^{18}F$]$F^-$ was collected by purging the proton irradiated target content (98% $^{18}O$—$H_2O$) over a QMA (Waters, Milford USA) cartridge. Next the QMA cartridge was eluted, using $CH_3CN$/water (700 μL of 95/5 v/v) containing Kryptofix 222 (26 mg) and $K_2CO_3$ (2.5 mg) to the reaction vial. The solution was dried under a gentle helium flow at 110° C. for 6 min, followed twice by an addition of $CH_3CN$ (1 mL) and dried under helium at 110° C. for 5 min each. For the standard conditions the mesyl precursor (2 mg) in dry DMSO (0.5 mL) was added, and reacted for 10 min at 120° C. The r.m. was diluted and [$^{18}F$]-1 or [$^{18}F$]-2 was subsequently purified using HPLC method A. The collected fraction was then passed over a sterile millex GV filter, and was further diluted with saline to a concentration of 10% EtOH.

The conversion was of 50-80% (as rough estimate) according to TLC. A fraction of the non converted alcohol precursor was always present in the precursor mixture used for the radiosynthesis, as well as some side products. The radiochemical yields starting from this mesylated precursor mixture are 5-35% for [$^{18}F$]-1 and 20-40% for [$^{18}F$]-2, under the standard conditions. Under these standard conditions also the bromo precursors were tested, however yield were always <3%. The radiochemical purity was always >95% and specific activity at end of synthesis was 165±83 GBq/μmol for [$^{18}F$]-1, and 138±37 GBq/μmol for [$^{18}F$]-2.

Analytical Part

Melting Points:

Values are peak values, and are obtained with experimental uncertainties that are commonly associated with this analytical method.

DSC823e (A): For a number of compounds, melting points were determined with a DSC823e (Mettler-Toledo) apparatus. Melting points were measured with a temperature gradient of 10° C./minute. Maximum temperature was 300° C. Values are peak values.

Mettler Toledo Mettler FP 81HT/FP90 apparatus (B): For a number of compounds, melting points were determined in open capillary tubes on a Mettler FP 81HT/FP90 apparatus. Melting points were measured with a temperature gradient of 1, 3, 5 or 10° C./minute. Maximum temperature was 300° C. The melting point was read from a digital display.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+$NH_4$]$^+$, [M+HCOO]$^-$, [M+$CH_3$COO]$^-$ etc . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" Single Quadrupole Detector, "MSD" Mass Selective Detector, "QTOF" Quadrupole-Time of Flight, "rt" room temperature, "BEH" bridged ethylsiloxane/silica hybrid, "CSH" charged surface hybrid, "UPLC" Ultra Performance Liquid Chromatography, "DAD" Diode Array Detector.

TABLE 1

LC-MS Methods (Flow expressed in mL/min; column temperature (T) in ° C.; Run time in min).

| Method | Instrument | Column | Mobile phase | Gradient | Flow Col T | Run time |
|---|---|---|---|---|---|---|
| 1 | Waters: Acquity ® UPLC ®-DAD/SQD | Waters: CSH ™ C18 (1.7 μm, 2.1 × 50 mm) | A: 95% CH$_3$COONH$_4$ 6.5 mM + 5% CH$_3$CN, B: CH$_3$CN | From 95% A to 40% A in 1.2 min, to 5% A in 0.6 min, held for 0.2 min | 1 50 | 5 |
| 2 | Waters: Acquity ® IClass UPLC ®-DAD/Xevo G2-S QTOF | Waters: CSH ™ C18 (1.7 μm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |

(*) Different MS tuning parameters (due to low sensitivity or ionization mode)

TABLE 2

Analytical data - melting point (M.p.) and LCMS: [M + H]$^+$ means the protonated mass of the free base of the compound, [M − H]$^−$ means the deprotonated mass of the free base of the compound or the type of adduct specified [M + CH$_3$COO]$^−$). R$_t$ means retention time (in min). For some compounds, exact mass was determined.

| Co. No. | M.p. (° C.) | [M + H]$^+$ | R$_t$ | LCMS Method |
|---|---|---|---|---|
| P-3 | 153.23 (A) | 442.1494 (+0.3 mDa) | 1.71 | 2 |
| [$^{19}$F]-2 | n.d. | 444.1454 (+0.7 mDa) | 2.21 | 2 |
| P-1 | 211.51 (A) | 442.1496 (+0.5 mDa) | 1.91 | 2 |
| [$^{19}$F]-1 | 187.28 (A) | 444.1451 (+0.4 mDa) | 2.29 | 2 |
| P-4 | n.d. | 504.0653 (+0.6 mDa) | 2.40 | 2 |
| P-2 | n.d. | 502 [M + H]$^−$ | 1.28 | 1 | n.d. means not determined.

Optical Rotations

Optical rotations were measured on a Perkin-Elmer 341 polarimeter with a sodium lamp and reported as follows: [α]° (λ, c g/100 ml, solvent, T° C.). [α]$_λ^T$=(100α)/(l×c): where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 mL).

TABLE 3

| | | | Optical Rotation data. | | |
|---|---|---|---|---|---|
| Co. No. | α$_D$ (°) | Wavelength (nm) | Concentration w/v % | Solvent | Temp. (° C.) |
| P-3 | +12.6 | 589 | 0.51 | DMF | 20 |
| [$^{19}$F]-2 | +12.7 | 589 | 0.58 | DMF | 20 |
| P-1 | +8.8 | 589 | 0.52 | DMF | 20 |
| [$^{19}$F]-1 | +85.6 | 589 | 0.54 | DMF | 20 |

NMR

For a number of compounds, $^1$H NMR spectra were recorded on a Bruker DPX-400 spectrometer operating at 400 MHz or on a Bruker Avance I spectrometer operating at 500 MHz, using CHLOROFORM-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 4

$^1$H NMR results

| Co. No. | $^1$H NMR result |
|---|---|
| [$^{19}$F]-1 | $^1$H NMR (400 MHz,, CDCl$_3$) δ ppm 1.71 (d, J = 6.5 Hz, 3 H) 3.97 (dd, J = 12.7, 7.4 Hz, 1 H) 4.24 (dd, J = 12.7, 4.2 Hz, 1 H) 4.66 (s, 2 H) 4.69-4.78 (m, 1 H) 5.60 (d, J = 46.9 Hz, 2 H) 6.60 (s, 1 H) 7.52 (d, J = 8.6 Hz, 2 H) 7.71 (d, J = 9.0 Hz, 2 H) 7.73 (s, 1 H) 8.22 (s, 1 H) |
| [$^{19}$F]-2 | $^1$H NMR (400 MHz, CDCl$_3$) δ ppm 1.71 (d, J = 6.5 Hz, 3 H) 3.99 (dd, J = 12.7, 7.4 Hz, 1 H) 4.26 (dd, J = 12.5, 4.2 Hz, 1 H) 4.59 (br s, 2 H) 4.74 (quind, J = 6.7, 6.7, 6.7, 6.7, 4.4 Hz, 1 H) 5.63 (d, J = 46.7 Hz, 2 H) 6.43 (dd, J = 8.6, 0.7 Hz, 1 H) 7.49-7.54 (m, 1 H) 7.57 (dd, J = 8.6, 2.3 Hz, 1 H) 7.67 (br s, 1 H) 7.74 (d, J = 8.5 Hz, 1 H) 7.75 (s, 1 H) 8.27 (dd, J = 2.2, 0.6 Hz, 1 H) |
| P-4 | $^1$H NMR (500 MHz, CDCl$_3$) δ ppm 1.72 (d, J = 6.6 Hz, 3 H) 3.99 (dd, J = 12.4, 7.5 Hz, 1 H) 4.24 (dd, J = 12.6, 4.2 Hz, 1 H) 4.66 (s, 2 H) 4.66 (br s, 2 H) 4.70-4.78 (m, 1 H) 6.44 (dd, J = 8.5, 0.7 Hz, 1 H) 7.45 (dd, J = 8.5, 1.3 Hz, 1 H) 7.57 (dd, J = 8.7, 2.3 Hz, 1 H) 7.66 (d, J = 1.7 Hz, 1 H) 7.71 (d, J = 8.7 Hz, 1 H) 7.75 (s, 1 H) 8.26 (dd, J = 2.2, 0.7 Hz, 1 H) |
| P-3 | $^1$H NMR (400 MHz, CDCl$_3$) δ ppm 1.70 (d, J = 6.5 Hz, 3 H) 2.17 (br s, 1 H) 3.98 (dd, J = 12.7, 7.2 Hz, 1 H) 4.25 (dd, J = 12.7, 4.2 Hz, 1 H) 4.59 (br s, 2 H) 4.72 (quind, J = 6.6, 6.6, 6.6, 6.6, 4.4 Hz, 1 H) 4.92 (s, 2 H) 6.43 (d, J = 8.6 Hz, 1 H) 7.42 (dd, J = 8.4, 1.3 Hz, 1 H) 7.56 (dd, J = 8.6, 2.3 Hz, 1 H) 7.70 (d, J = 8.3 Hz, 1 H) 7.74 (s, 1 H) 7.79 (s, 1 H) 8.26 (d, J = 1.6 Hz, 1 H) |
| P-1 | $^1$H NMR (500 MHz, CDCl$_3$) δ ppm 1.71 (d, J = 6.6 Hz, 3 H) 3.98 (dd, J = 12.7, 7.5 Hz, 1 H) 4.21 (br s, 1 H) 4.24 (dd, J = 12.7, 4.0 Hz, 1 H) 4.60-4.68 (m, 4 |

TABLE 4-continued

$^1$H NMR results

| Co. No. | $^1$H NMR result |
|---|---|
| | H) 4.73 (quind, J = 6.6, 6.6, 6.6, 6.6, 4.3 Hz, 1 H) 6.47 (s, 1 H) 7.51 (d, J = 8.4 Hz, 2 H) 7.70 (d, J = 8.4 Hz, 2 H) 7.74 (s, 1 H) 8.24 (s, 1 H) |

Binding Assay

For [$^3$H]-compound A (a NAM compound, selective for mGlu2/3 (~20 fold selective for 2 over 3) vs other mGluRs) binding, membranes from human mGlu2 and mGlu3 HEK293 cells, and also rat cortical membranes, were used. After thawing, membranes were homogenized using an Ultra Turrax homogenizer and suspended in ice-cold binding buffer containing 50 mM Tris-HCl (pH 7.4), 10 mM MgCl$_2$, 2 mM CaCl$_2$. Displacement studies were done using 6 nM of radioligand, except for human mGlu3 membranes where 25 nM was used. Assay mixtures were incubated for 60 min at RT in a volume of 0.5 ml containing 7.5 mg, 75-100 mg or 75 μg membrane protein of human mGlu2, human mGlu3 or rat cortex, respectively. Non-specific binding was estimated in the presence of 10 mM compound B (a NAM with IC$_{50\sim10}$ nM against hmGlu2 and IC$_{50}$~200 nM against hmGlu3). Filtration was performed using Whatman GF/C filter sheets pre-soaked in 0.1% PEI and a Brandell harvester 96.

Filters from filters sheets were punched into vials. After the addition of scintillation liquid, radioactivity on the filters was counted in a Liquid Scintillation Analyzer from Perkin Elmer.

Radioligand competition binding data were calculated as percentage of total binding measured in the absence of test compound. Inhibition curves, plotting percentage of total binding versus the log concentration of the test compound, were generated using the Lexis software. Sigmoid inhibition curves were analyzed using non-linear regression analysis.

TABLE 5

Binding data for compounds 1 and 2.

| Compound | Protocol | pIC$_{50}$ | Eff Curve |
|---|---|---|---|
| 1 | Glu2 HEK293 | 8.56 | 93 |
| 2 | Glu2 HEK293 | 8.55 | 94 |
| 1 | Glu3 HEK293 | 8.14 | 104 |
| 2 | Glu3 HEK293 | 8.36 | 107.5 |
| 1 | Glu2-3 rat cortex | 8.78 | 95 |

Biodistribution Studies

General

Animal PET imaging was performed on a lutetium oxyorthosilicate detector-based tomograph (microPET FOCUS-220; Siemens Medical Solutions USA, Knoxville, Tenn.), which had a transaxial resolution of 1.35 mm (full-width at half-maximum). Data were acquired in a 128×128×95 matrix with a pixel width of 0.475 mm and a slice thickness of 0.796 mm. During PET imaging, rats were kept under gas anesthesia (2.5% isoflurane in oxygen at a flow rate of 1 l/min), and their body temperature was maintained between 36.5 and 37° C. using a heating pad. PET data were analyzed using Pmod software version 3.2 (Pmod, Zurich Switzerland).

Sprague-Dawley rats obtained from Harlan (the Netherlands), were housed in groups of four to six per cage until treatment. They were kept at a constant temperature of 21° C. and at a 12-h light/dark cycle, in which lights were switched on at 8:00 a.m. Animals had unrestricted access to food (Teklad Global 16% Protein Rodent Diet, Harlan, Madison, Wis., USA) and water. All animal experiments were performed in compliance with Belgium laws on animal experimentation and after approval by the local animal ethics committee.

Ex-Vivo Biodistribution

The biodistribution of [$^{18}$F]-1 was determined at 2, 10, 30 and 60 min, after injection in Sprague Dawley (SD) rats (n=3 per time point) while for [$^{18}$F]-2 the 30 min time point was not performed. Rats were injected intravenously with 0.7-1.1 MBq via a tail vein and euthanized at the time points indicated above, under isoflurane anesthesia. All tissues were dissected, weighed and counted for radioactivity in a gamma counter.

The biodistribution of [$^{18}$F]-1 was determined at 2, 10, 30 and 60 min, after injection in Sprague Dawley rats (n=3 per time point). Rats were injected intravenously with 0.7-1.1 MBq via a tail vein and euthanized at the time points indicated above, under isoflurane anesthesia. All tissues were dissected, weighed and counted for radioactivity in a gamma counter.

The biodistribution of [$^{18}$F]-1 showed the highest uptake in the liver with a washout observed in all peripheral organs, while bone uptake goes slightly up over time. In addition muscle uptake is low and appears to stabilize over time.

The brain uptake for [$^{18}$F]-1 was very high, while showing an increased uptake over time for all areas in the brain except for the pons, of which the uptake is rather stable over time. The highest uptake was observed in the cortex followed by the striatum, the pons showed the lowest brain uptake.

TABLE 6

Biodistribution data of [$^{18}$F]-1 depicted in SUV ± SD.

| Organ | Mean 2 min | SD 2 min | Mean 10 min | SD 10 min | Mean 30 min | SD 30 min | Mean 60 min | SD 60 min |
|---|---|---|---|---|---|---|---|---|
| kidneys | 4.97 | 0.94 | 2.58 | 0.07 | 2.08 | 0.27 | 2.16 | 0.25 |
| liver | 9.74 | 1.32 | 6.38 | 0.33 | 4.66 | 0.36 | 4.75 | 0.99 |
| spleen | 2.81 | 0.52 | 1.68 | 0.06 | 1.06 | 0.14 | 1.02 | 0.46 |
| pancreas | 4.30 | 0.58 | 2.36 | 0.33 | 2.06 | | 2.33 | 0.48 |
| lungs | 2.93 | 0.41 | 1.78 | 0.43 | 1.63 | 0.26 | 1.92 | 0.17 |
| heart | 3.54 | 0.64 | 2.11 | 0.16 | 1.41 | 0.13 | 1.30 | 0.09 |
| striatum | 1.98 | 0.21 | 3.46 | 0.17 | 4.15 | 0.72 | 7.12 | 0.19 |
| hippocampus | 1.53 | 0.14 | 2.49 | 0.24 | 3.10 | 0.70 | 3.90 | 0.28 |
| pons | 1.53 | 0.14 | 1.73 | 0.12 | 1.76 | 0.33 | 1.85 | 0.31 |
| cortex | 3.50 | 0.54 | 8.37 | | 6.96 | 1.76 | 8.11 | 0.32 |
| rest of cerebrum | 2.06 | 0.28 | 3.34 | 0.13 | 4.37 | 0.99 | 5.52 | 0.39 |
| whole cerebrum | 1.96 | 0.23 | 3.05 | 0.17 | 3.94 | 0.85 | 5.00 | 0.21 |
| cerebellum | 2.25 | 0.34 | 3.17 | 0.12 | 3.93 | 0.94 | 4.41 | 0.04 |
| blood | 1.12 | 0.07 | 0.74 | 0.05 | 0.47 | 0.03 | 0.50 | 0.03 |
| cerebrum + cerebellum | 2.03 | 0.25 | 3.11 | 0.16 | 3.98 | 0.86 | 4.95 | 0.17 |
| bone | 0.39 | 0.13 | 0.34 | 0.01 | 0.48 | 0.04 | 0.58 | 0.03 |
| muscle | 0.50 | 0.03 | 0.83 | 0.04 | 0.75 | 0.04 | 0.79 | 0.20 |

The biodistribution of [$^{18}$F]-2 showed a high uptake in the liver, and a medium brain uptake in the cerebrum and cerebellum. All regions showed washout, with the exception of the bone, which showed an increase of uptake over time. The brain uptake of [$^{18}$F]-2 showed a variable tracer concentration with slow washout in the studied regions. The highest uptake was observed in the cortex, and the lowest brain uptake in the pons.

TABLE 7

Biodistribution data of [$^{18}$F]-2 depicted in SUV ± SD.

| Organ | Mean 2 min | SD 2 min | Mean 10 min | SD 10 min | Mean 60 min | SD 60 min |
|---|---|---|---|---|---|---|
| kidneys | 4.05 | 0.78 | 2.73 | 0.18 | 1.81 | 0.13 |
| liver | 8.44 | 2.09 | 6.22 | 0.06 | 2.83 | 0.18 |
| spleen | 2.53 | 0.38 | 1.36 | 0.09 | 0.87 | 0.00 |
| pancreas | 3.29 | 0.38 | 2.06 | 0.40 | 1.27 | 0.26 |
| lungs | 2.66 | 1.87 | 1.52 | 0.07 | 1.02 | 0.17 |
| heart | 2.42 | 0.36 | 1.67 | 0.09 | 0.82 | 0.05 |
| striatum | 1.51 | 0.04 | 1.61 | 0.26 | 1.30 | 0.26 |
| hippocampus | 1.03 | 0.06 | 1.17 | 0.24 | 0.74 | 0.06 |
| pons | 1.04 | 0.03 | 0.74 | 0.15 | 0.40 | 0.05 |
| cortex | 2.50 | 0.16 | 2.51 | 0.60 | 1.56 | 0.22 |
| rest of cerebrum | 1.45 | 0.08 | 1.39 | 0.23 | 0.97 | 0.22 |
| whole cerebrum | 1.39 | 0.04 | 1.34 | 0.19 | 0.90 | 0.14 |
| cerebellum | 1.53 | 0.01 | 1.23 | 0.23 | 0.73 | 0.05 |
| blood | 0.96 | 0.20 | 0.92 | 0.06 | 0.67 | 0.02 |
| cerebrum + cerebellum | 1.44 | 0.06 | 1.34 | 0.21 | 0.89 | 0.13 |
| bone | 0.53 | 0.10 | 0.62 | 0.13 | 2.77 | 0.03 |
| muscle | 0.88 | 0.16 | 0.82 | 0.07 | 0.59 | 0.10 |

Pet Scanning

All pretreatment solutions were 1 mg/mL solutions in 20% β-cyclodextrine in saline with a pH ranging between 6 and 8, and sterile filtered over a Millex GV filter prior to use.

For the baseline scan, 36-43 MBq of [$^{18}$F]-1 was injected in 3 SD rats weighing 229-251 g in the tail vein, and scanned simultaneously during a 90 min dynamic PET scan. For the pretreatment scan using compound A (a NAM compound, selective for mGlu2/3 (~20 fold selective for 2 over 3) vs other mGluRs), the same animals were injected with 10 mg/kg compound A s.c. 60 minutes prior to injection of 38-37 MBq [$^{18}$F]-1 in the tail vein, and scanned simultaneously during a 90 minutes dynamic PET scan.

A high brain uptake was observed for [$^{18}$F]-1, and especially the frontal cortex and the striatum show a high uptake. The uptake was the lowest in the pons, while the uptake of the pons was in the same range after pretreatment with compound A. In the other regions the uptake was reduced after pretreatment with compound A. The peak uptake was probably not reached within 90 min, since the time activity curves kept on increasing as a function of time post injection.

For the baseline scan, 39-49 MBq of [$^{18}$F]-2 was injected in 3 SD rats weighing 301-310 g in a tail vein, and scanned simultaneously during a 90-min dynamic PET scan. For the pretreatment scan using compound A, the same animals were injected with 10 mg/kg compound A s.c. 60 min prior to injection of 46-50 MBq [$^{18}$F]-2 in the tail vein, and scanned simultaneously during a 90 min dynamic PET scan.

Figure 4:
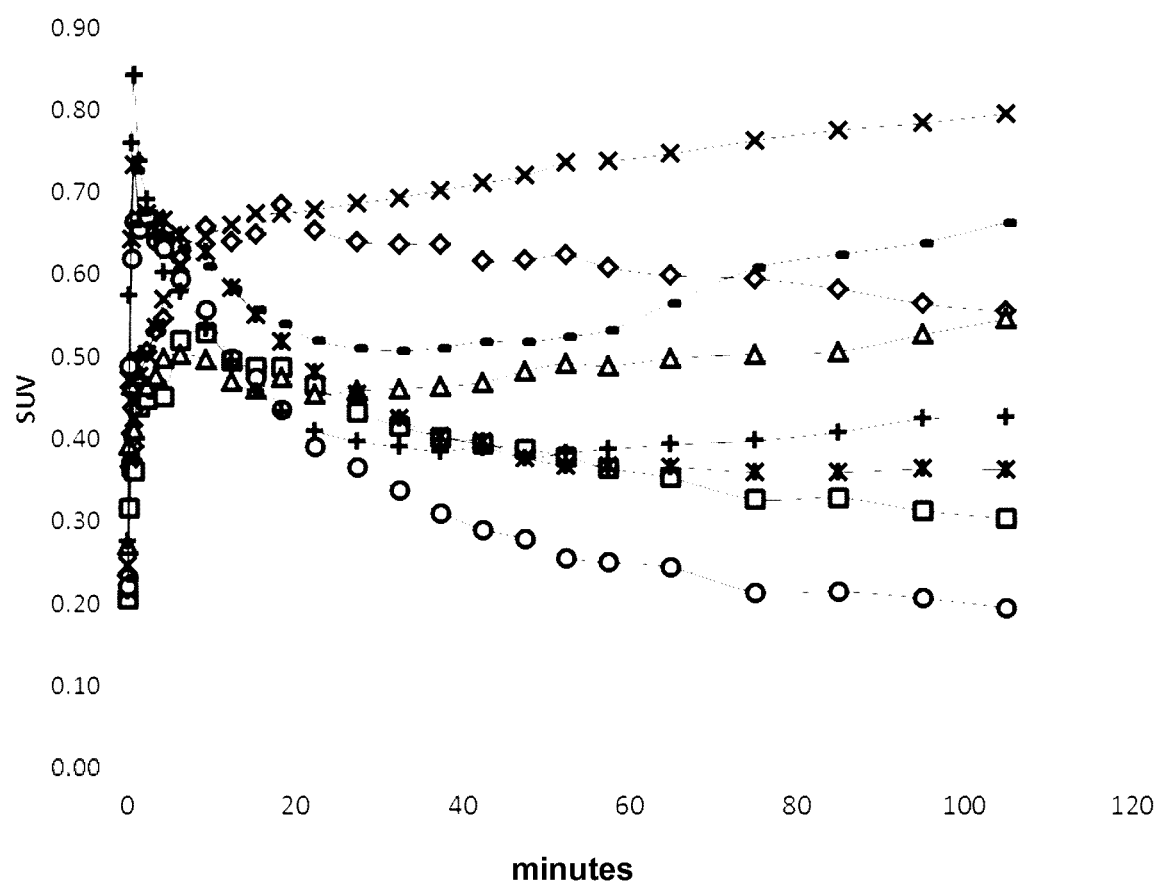
FIG. 4 shows the time activity curves for the uptake of [¹⁸F]-2 with and without treatment of compound A (a NAM compound, selective for mGlu2/3 (~20 fold selective for 2 over 3) vs other mGluRs), indicated in the figure as mGlu2/3 NAM in SD rats.

The µPET scans obtained after injection of [$^{18}$F]-2 (FIG. 4), showed some mixed results. The peak uptake was higher after pretreatment, but generally showed a faster washout, while the uptake of the brain regions at the baseline scan did not show this early peak. In addition the cortex showed an increase of uptake over time, which might be due to partial volume effects from skull that due to tracer defluorination showed high and increasing radioactivity concentration.

Discussion

The uptake in the periphery of the ex-vivo biodistribution showed the highest uptake in the liver, as well as a high kidney uptake, followed by urinary excretion. The bone uptake [$^{18}$F]-1 was low at start, but increased slightly up over time hinting for some defluorination. [$^{18}$F]-2 showed substantial increase of bone uptake over time, indicating massive defluorination, with subsequent binding of [$^{18}$F]F$^-$ to bone.

The ex-vivo biodistribution showed a high brain uptake for [$^{18}$F]-2, followed by [$^{18}$F]-1. [$^{18}$F]-2 showed a fast washout from the different brain areas. The pons is considered to be a reference region as with absence of mGluR2 or mGluR3 expression, while on all other regions both mGluR2 and mGluR3 are present, with the highest expression levels in the cerebral cortex (Farinha A. et al. BJPharmacol, 2015, 172, 2383-2396). [$^{18}$F]-2 showed the highest uptake in the cortex, with a low uptake in the pons in combination with a faster washout from the pons compared to the other regions, and suggesting a good mGluR2/3 specificity, since the brain uptake reflects the reported distribution pattern for mGluR2/3. [$^{18}$F]-1 also showed a high uptake in the cortex and a low uptake in the pons, however tracer concentration continued to increase over time for all brain regions, except for the pons, where the uptake appears rather stable. Still the uptake pattern matches the distribution pattern for mGluR2/3 quite well. The increased uptake is hinting for either a very high affinity or (pseudo) irreversible binding of [18F]-1. µPET scan after injection of [$^{18}$F]-2, showed high brain uptake and faster washout from frontal cortex after compound A pretreatment compared to the baseline scan, indicating mGluR2/3 specific binding. The high bone uptake was however causing significant partial volume effects, and a spillover of signal from the bone was especially observed in the cortex, which is located near the skull, but also contains a high expression of mGluR2/3.

In the PET scans, [$^{18}$F]-1 showed peculiar brain kinetics with persistently increasing activity concentration in the frontal cortex and the striatum as a function of time whereas activity in the pons remained low. The high uptake in frontal cortex and hippocampus could be blocked by pretreatment with compound A. This continuous uptake pattern might be due to a high affinity of [$^{18}$F]-1 for either or both mGluR2 and mGluR3, or could be due to (pseudo)irreversible binding. These data also indicate good mGluR2/3 specificity, since the uptake in all brain regions was reduced by compound A pretreatment to about the same height as the uptake in the pons.

The invention claimed is:

1. A compound according to Formula (I)

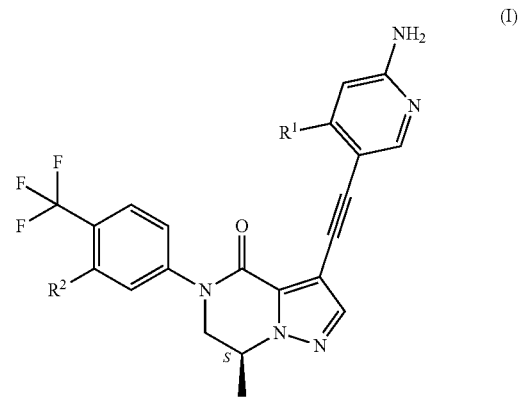

wherein R¹ is —CH₂F and R² is —H, or R¹ is —H and R² is —CH₂F, and wherein at least one atom is radioactive, or a pharmaceutically acceptable salt or a solvate thereof, for use in imaging or quantifying mGlu2 and 3 receptors.

2. The compound according to claim 1, having the Formula

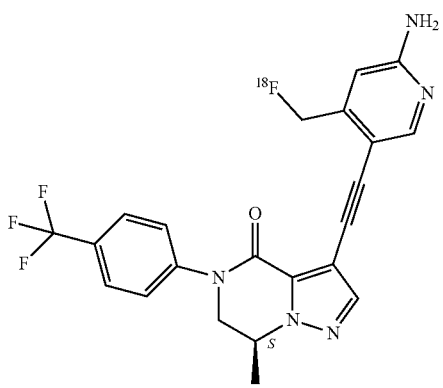

or a pharmaceutically acceptable salt or a solvate thereof.

3. The compound according to claim 1, having the Formula

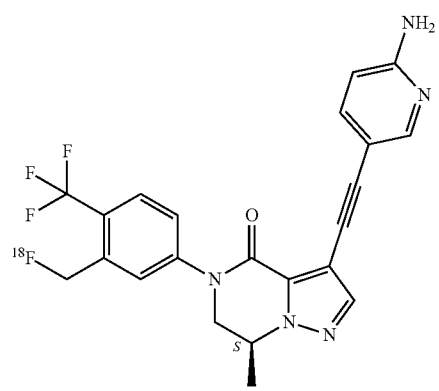

or a pharmaceutically acceptable salt or a solvate thereof.

4. A radiolabelled compound of Formula

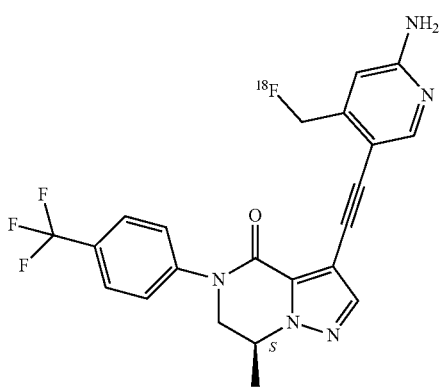

or a pharmaceutically acceptable salt or a solvate thereof.

5. A radiolabelled compound of Formula

or a pharmaceutically acceptable salt or a solvate thereof.

6. A sterile pharmaceutical composition comprising a compound of Formula (I) as defined in claim 1, or a pharmaceutically acceptable salt or a solvate thereof, and a pharmaceutically acceptable carrier or diluent.

7. A method of imaging a tissue, cells or a mammal, comprising contacting with a detectable amount of a compound of Formula (I) or a pharmaceutically acceptable salt or a solvate thereof as defined in claim 1, to a tissue, cells or mammal and detecting the labelled compound associated with the mGlu2 and 3 receptor.

8. The method according to claim 7 wherein the imaging technique is positron-emission tomography.

9. A compound selected from the group consisting of

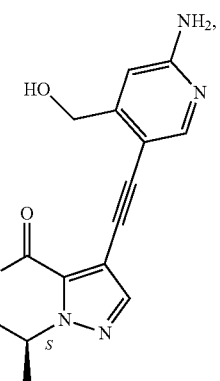
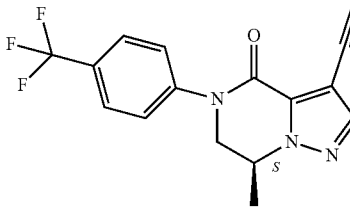

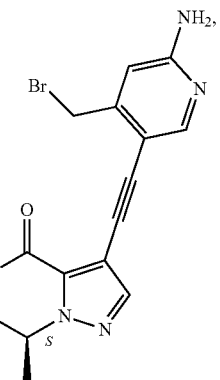
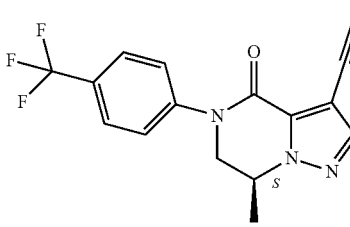

-continued

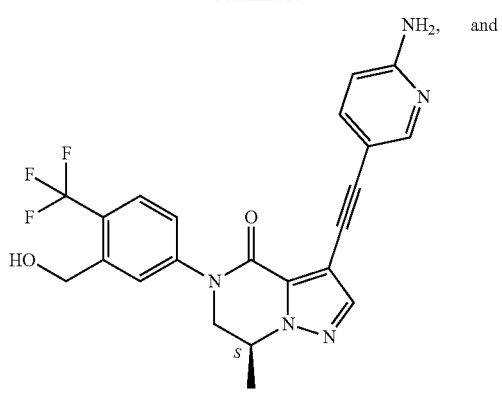

or a pharmaceutically acceptable salt or a solvate thereof.

10. A process for the synthesis of the compound defined in claim 2, comprising (a) the steps of (a-1) reacting a compound of Formula (P-1) with methanesulfonic anhydride in the presence of a base and an inert solvent, and (a-2) reacting the compound obtained in step (a-1) with [$^{18}$F]F$^-$ in the presence of a base in an inert solvent

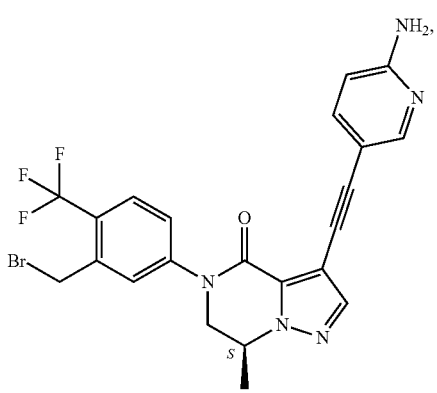

P-1

-continued

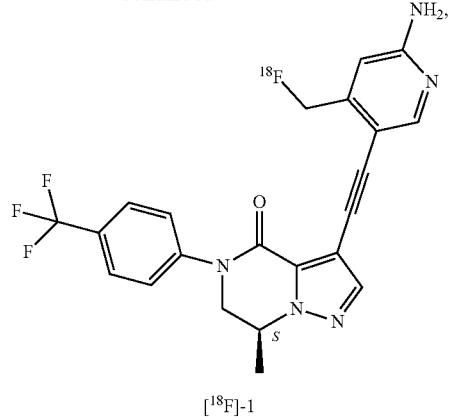

[$^{18}$F]-1 or
(b) the step of reacting a compound of Formula (P-2) with [$^{18}$F]F$^-$ in the presence of a base in an inert solvent

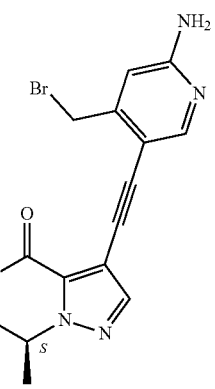

P-2

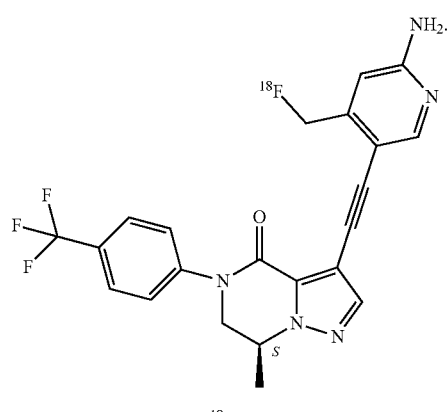

[$^{18}$F]-1

11. A process for the synthesis of the compound defined in claim 3, comprising (a) the steps of (a-1) reacting a compound of Formula (P-3) with methanesulfonic anhydride in the presence of a base and an inert solvent, and (a-2) reacting the compound obtained in step (a-1) with a nucleophilic radioactive fluorinating reagent [$^{18}$F]F$^-$ in the presence of a base in an inert solvent

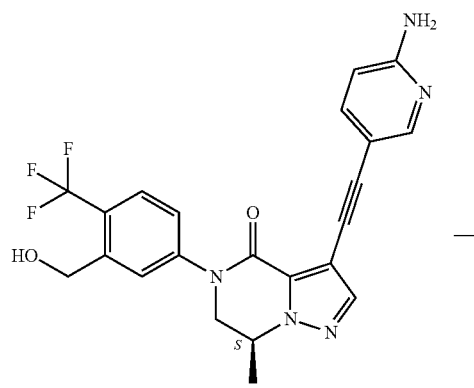
P-3
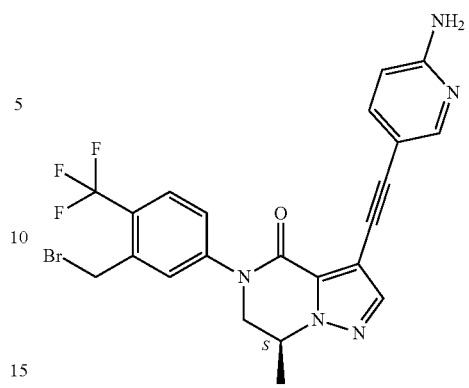
P-4
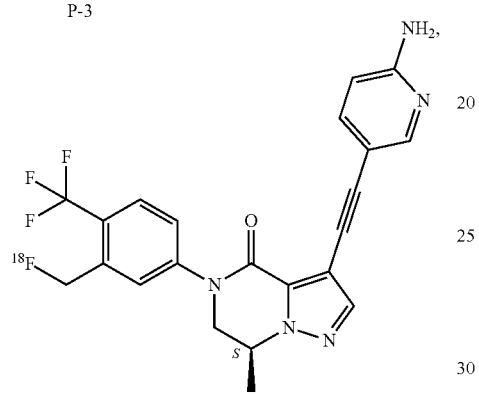
[¹⁸F]-2
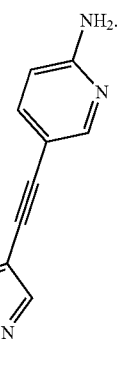
[¹⁸F]-2
or
(b) the step of reacting a compound of Formula (P-4) with a nucleophilic radioactive fluorinating reagent [$^{18}$F]F$^-$ in the presence of a base in an inert solvent
12. The process according to claim 11, wherein in step (a-1) the base is trimethylamine or triethylamine and the inert solvent is dichloromethane.
\* \* \* \* \*